US008758740B2

(12) United States Patent
Kuriyama

(10) Patent No.: US 8,758,740 B2
(45) Date of Patent: Jun. 24, 2014

(54) COMPOSITION FOR PROMOTING KETONE BODY PRODUCTION

(75) Inventor: Masaki Kuriyama, Kyoto (JP)

(73) Assignee: Earthus, Inc, Kyoto (JP)

( * ) Notice: Subject to any disclaimer, the term of this patent is extended or adjusted under 35 U.S.C. 154(b) by 500 days.

(21) Appl. No.: 12/450,510

(22) PCT Filed: Mar. 31, 2008

(86) PCT No.: PCT/JP2008/056338
§ 371 (c)(1),
(2), (4) Date: Mar. 15, 2010

(87) PCT Pub. No.: WO2008/120778
PCT Pub. Date: Oct. 9, 2008

(65) Prior Publication Data
US 2010/0210726 A1    Aug. 19, 2010

(30) Foreign Application Priority Data

Mar. 30, 2007   (JP) ................................ 2007-089973

(51) Int. Cl.
*A61K 31/74*         (2006.01)
(52) U.S. Cl.
USPC ................... 424/78.08; 424/78.17; 424/78.37
(58) Field of Classification Search
CPC ... A61K 31/74; A61K 31/765; A61K 31/785; A61K 2201/30
See application file for complete search history.

(56) References Cited

U.S. PATENT DOCUMENTS

| | | | | |
|---|---|---|---|---|
| 5,206,341 | A * | 4/1993 | Ibay et al. ..................... | 528/361 |
| 5,229,158 | A * | 7/1993 | Yalpani ......................... | 426/565 |
| 6,207,217 | B1 * | 3/2001 | Peoples et al. ................. | 426/635 |
| 2003/0054550 | A1 * | 3/2003 | Baker et al. .................... | 435/368 |
| 2006/0275253 | A1 | 12/2006 | Ushida et al. | |
| 2006/0280721 | A1 * | 12/2006 | Veech et al. ............... | 424/78.37 |

FOREIGN PATENT DOCUMENTS

| | | |
|---|---|---|
| CN | 1729965 | 2/2006 |
| CN | 1778904 | 5/2006 |
| EP | 0 780 123 | 6/1997 |
| JP | 10-095730 | 4/1998 |
| JP | 2000-515510 | 11/2000 |
| JP | 2001-515510 | 9/2001 |
| JP | 2002-521330 | 7/2002 |
| JP | 2002-524506 | 8/2002 |
| JP | 2003-509366 | 3/2003 |
| WO | 98/02148 | 1/1998 |
| WO | 98/41200 | 9/1998 |
| WO | 00/04895 | 2/2000 |
| WO | 00/15216 | 3/2000 |
| WO | 01/19361 | 3/2001 |
| WO | 2004/108740 | 12/2004 |
| WO | 2005/021013 | 3/2005 |

OTHER PUBLICATIONS http://en.wikipedia.org/wiki/Treatment of Parkinson%27s_disease, Jan. 10, 2012.*
http://consensus.nih.gov/2010/alzstatement.htm, Apr. 2010.*
International Search Report issued May 20, 2008 in International (PCT) Application No. PCT/JP2008/056338.
M. Vincenzini et al., "Occurrence of Poly-β-Hydroxybutyrate in *Spirulina* Species", Journal of Bacteriology, vol. 172, No. 5, pp. 2791-2792, May 1990.
M. Gasior et al., "Neuroprotective and Disease-Modifying Effects of the Ketogenic Diet", Behavioural Pharmacology, vol. 17, No. 5-6, p. 431-439, Sep. 2006.
B. A. Ramsay et al., "Production of Poly-(β-Hydroxybutyric-Co-β-Hydroxyvaleric) Acids", Applied and Environmental Microbiology, vol. 56, No. 7, pp. 2093-2098, Jul. 1990.
R. L. Veech, "The Therapeutic Implications of Ketone Bodies: The Effects of Ketone Bodies in Pathological Conditions: Ketosis, Ketogenic Diet, Redox States, Insulin Resistance, and Mitochondrial metabolism", Prostaglandins, Leukotrienes and Essential Fatty Acids, vol. 70, pp. 309-319, 2004.
A. J. Rich, "Ketone Bodies as Substrates", Proceedings of the Nutrition Society, vol. 49, pp. 361-373, 1990.
A. J. Anderson et al., "Occurrence, Metabolism, Metabolic Role, and Industrial Uses of Bacterial Polyhydroxyalkanoates", Microbiological Reviews, vol. 54, No. 4, pp. 450-472, Dec. 1990.
S. Y. Lee, "Bacterial Polyhydroxyalkanoates", Biotechnology and Bioengineering, vol. 49, pp. 1-14, 1996.
S. C. Slater et al., "Cloning and Expression in *Escherichia coli* of the *Alcaligenes eutrophus* H16 Poly-β-Hydroxybutyrate Biosynthetic Pathway", Journal of Bacteriology, vol. 170, No. 10, pp. 4431-4436, Oct. 1988.
P. Schubert et al., "Cloning of the *Alcaligenes eutrophus* Genes for Synthesis of Poly-β-Hydroxybutyric Acid (PHB) and Synthesis of PHB in *Escherichia coli*", Journal of Bacteriology, vol. 170, No. 12, pp. 5837-5847, Dec. 1988.
Y. Poirier et al., "Polyhydroxybutyrate, A Biodegradable Thermoplastic, Produced in Transgenic Plants", Science, vol. 256, pp. 520-523, Apr. 24, 1992.

(Continued)

*Primary Examiner* — James Rogers
(74) *Attorney, Agent, or Firm* — Wenderoth, Lind & Ponack, L.L.P.

(57) ABSTRACT

Provided is a composition for promoting ketone body production that comprises a water insoluble polymer of a β-hydroxy short-medium chain fatty acid such as homopolymer of β-hydroxybutyric acid or a copolymer of β-hydroxybutyric acid and β-hydroxyvaleric acid. The composition is useful for the treatment or prevention of a disease or condition that can be treated by promoting ketone body production.

15 Claims, No Drawings

(56) References Cited

OTHER PUBLICATIONS

M. Marounek et al., "Age Effect on In Vitro Fermentation Pattern and Methane Production in the Caeca of Chickens", Physiol. Res. vol. 47, pp. 259-263, 1998.

D. Jamroz et al., "Digestibility and Energy Value of Non-Starch Polysaccharides in Young Chickens, Ducks and Geese, Fed Diets Containing High Amounts of Barley", Comparative Biochemistry and Physiology Part A, vol. 131, pp. 657-668, 2002.

M. Kihara et al., "Production of Short-Chain Fatty Acids and Gas from Various Oligosaccharides by Gut Microbes of Carp (*Cyprinus carpio* L.) in Micro-Scale Batch Culture", Comparative Biochemistry and Physiology Part A, vol. 132, pp. 333-340, 2002.

D. O. Mountfort et al., "Hindgut Fermentation in Three Species of Marine Herbivorous Fish", Applied and Environmental Microbiology, vol. 68, No. 3, pp. 1374-1380, Mar. 2002.

D. Seebach et al., "Isolation and $^1$H-NMR Spectroscopic Identification of Poly(3-hydroxybutanoate) from Prokaryotic and Eukaryotic Organisms", Eur. J. Biochem., vol. 224, pp. 317-328, 1994.

* cited by examiner

COMPOSITION FOR PROMOTING KETONE BODY PRODUCTION

This application is a U.S. national stage of International Application No. PCT/JP2008/056338 filed Mar. 31, 2008.

TECHNICAL FIELD

The present application provides a composition for promoting the production of ketone bodies and a method for promoting the production of ketone bodies.

BACKGROUND ART

"Ketone bodies" represent three compounds, acetone, acetoacetate and β-hydroxybutyrate that are produced in the liver by degrading fatty and released into the blood. Among the ketone bodies, acetone is very volatile and easily excreted in the expired air. Therefore, when measuring the amount of ketone bodies in the blood, total amount of acetoacetate and β-hydroxybutyrate in the blood is measured and represented as "total ketone bodies". Ketone bodies are used as energy source together with glucose, free fatty acids or amino acids, and are utilized in various organs other than liver, such as brain, heart, kidney and skeletal muscle. Ketone bodies are very important energy source especially for brain. In the brain, only glucose and ketone bodies can be utilized as energy sources. The physiological concentration of ketone bodies varies widely dependent on the diet, excise and the like in contrast with the concentrations of other factors that are maintained within relatively narrower ranges.

It has been known that high-fat, low-carbohydrate diet induces ketone bodies and is useful for the treatment of epilepsy. It has also been known that increasing of ketone body level in the blood by means of ketogenesis induction or administration of a ketone body can provide treating and/or preventing effect against various diseases For example, Non Patent Literature 1 discloses that mild ketosis, i.e. a mild elevation of blood ketone body level may offer therapeutic potential in a variety of conditions and diseases. Non Patent literature 1 reports that the ketogenic diet is effective for the prevention of seizures in patients with refractory epilepsy, weight loss and as adjuncts to cancer chemotherapy; that salts of ketone bodies are useful for the treatment of the decline of the concentrations of glucose, free fatty acids and glycerol in a patient receiving fluid therapy and for the treatment of genetic disease caused by the depression of acyl-CoA dehydrogenase. Further, it also reports that mild increase of the concentration of ketone bodies is effective for the treatment or prevention of: insulin resistance typical in type II diabetic patients, genetic defects of glucose transport and PHD activity; hypoglycemia; hypoxia; cardiomyopathy; hereditary muscular atrophy; diseases or conditions caused by free radicals including Parkinson's disease, and neurodegenerative disease such as Alzheimer's disease based on results of experiments using animal models.

In view of the above discussed reports, products that control ketone body level in the body have been proposed. One example of the products is a high-fat low-carbohydrate diet, i.e. a ketogenic diet. By receiving the ketogenic diet continuously, the ketogenesis in the liver is stimulated and the concentration of ketone bodies in the blood is increased. However, due to the continuous intake of the high-fat diet, the other diseases such as hyperlipidemia may be induced. In addition, no ketogenic diet product that provides satisfied taste has been provided and therefore, continuous intake of ketogenic diet is not preferable in view of QOL of the patient.

Another approach for controlling ketone body level in the body is to increase concentration of ketone bodies such as acetoacetate and D-β-hydroxybutyric acid in the blood by administering them intravenously (infusion), orally or enterally. However, administering those compounds that are acids directly in the blood is not preferable in view of keeping the blood pH around neutral. In addition, oral administration of an acid per se is difficult and therefore, derivatives of ketone bodies including salts, esters, cyclic oligomers, polymers and metabolic precursors thereof have been proposed (Patent Literatures 1-4 and Non-patent Literature 2).

Patent Literature 1 discloses that a precursor of a ketone body, such as an oligomer, polymer and ester thereof, can enhance the blood level of ketone bodies and is useful for increasing cardiac efficiency, treating diabetics and insulin resistant states and/or reversing, retarding or preventing the effects of neurodegenerative disorders and epilepsy. According to the Patent Literature 1, the number of the repeating units of the polymer may be 2 to 100 and the polymer used in the working example is an oligomer having an average degree of polymerization of 3.75 or a sodium salt of D-β-hydroxybutyric acid. 2M solution of the each was administered to a rat in an amount of 0.1 mL/100 g body weight and the blood β-hydroxybutyric acid level was monitored over 120 minutes from the administration. As a result, the highest blood β-hydroxybutyric acid level in the rat administered with the oligomer was observed at around 60 minutes after the administration, and the time was later than that when the highest β-hydroxybutyric acid level was observed in the rat received sodium salt of D-β-hydroxybutyric acid. At two hours from the administration, the blood hydroxybutyric acid level was increased 5-12 times of the normal level and concluded that those derivatives can significantly increase the blood level of ketone body for several hours from the administration.

Patent Literature 2 discloses that linear or cyclic oligomers or esters of D-β-hydroxybutyric acid can increase the blood level of hydroxybutyric acid and are effective for the reduction of protein catabolism, appetite suppression, the increase of cardiac efficiency, the treatment of diabetes and insulin resistant states, Alzheimer's disease, fronto-temporal degeneration associated with Pick's disease, vascular dementia, senile dementia of Lewy body type, dementia of Parkinsonism with frontal atrophy, progressive supranuclear palsy and corticobasal degeneration, Down's syndrome associated Alzheimer's disease, myasthenia gravis, and muscular dystrophy. In the working example, blood hydroxybutyric acid level in a dog given a single oral bolus of the cyclic trimer at 5% of the daily caloric requirement (i.e. 10 g of the cyclic trimer) was elevated. The highest level was more than 5 times of the normal level and was observed at 90 minutes from the administration. The blood level of hydroxybutyric acid was then gradually decreased over 6 hours (Example 2). In example 3, a dog was fed with 134.5 g of a mixture of meat (111 g) and the cyclic trimer (23.5 g) four times over 9 hours. The blood hydroxybutyric acid level was increased to about 50 times of the normal level within 30 minutes from the first administration. After the third administration (at 6 hours), the blood ketone body level was still 30 times of the normal level and by the next morning, returned to the normal level. Further, in Example 7, rats were fed with experimental diets containing 25% of the calories from oligomers having average molecular weight of 200 and 1000 respectively, for 5 days. The blood hydroxybutyric acid level was 9 times of the normal level in the rats fed with the oligomer of 200 MW and 2 times of the normal level in the rat fed with the oligomer of 1000 MW. Those results suggest that when the water solubility of the oligomer is decreased, the blood ketone body level will be decreased.

As discussed above, administration of the oligomer once will elevate the blood ketone body level several times within a short term and the elevated level will be kept for several hours.

Patent Literature 3 discloses to improve cerebral function by increasing blood ketone body level by means of administeration of a β-hydroxybutyric acid derivative or dimer to decamer (2-10 mer) of β-hydroxybutyric acid. Although Patent Literature 3 suggests that dimer to decamer (2-10 mer) of β-hydroxybutyric acid and esters or salts of β-hydroxybutyric acid monomer will provide similar effect on the blood ketone body level as well as on the cerebral function, only salt and ester of hydroxybutyric acid monomer were used in the working examples.

Patent Literature 4 discloses that cyclic ester of β-hydroxybutyric acid (3-hydroxybutyric acid) can elevate the blood level of ketone bodies that are β-hydroxybutyric acid and/or acetoacetate. The elevation of blood level of ketone bodies is effective for treating a cell that is subjected to malfunction due to action of free radicals, toxic agents such as peptides and proteins and genetic defects deleterious to cell metabolism, insulin resistance or other glucose metabolism defects or defect inducing states, ischemia, head trauma, and/or for increasing cell efficiency, and accordingly, is effective for the treatment of Alzheimer's disease, Parkinson's disease, amylotrophic lateral sclerosis, epilepsy, free radical disease, heart failure, Type II diabetes, deficiency or blocage of pyruvate dehydrogenase, inability to perform glycolysis in one or more cell types and Duchenne's muscular dystrophy. In Patent Literature 4, a working example in which a cyclic trimer was used as the cyclic oligomer was disclosed. At 80 minutes and 150 minutes after oral administration of the diet containing 11 wt % of the trimer, the blood level of ketone bodies were elevated to 1.8 times and 2.4 times of the normal level, respectively.

Non-patent literature 1 teaches the possibility for treating or preventing various diseases by administering ketone bodies directly into the blood by means of intravenous drip. Non-patent literature 2 teaches the possibility for increasing the blood level of ketone bodies by administering water soluble β-hydroxybutyric acid directly into the blood by means of intravenous drip. In addition it also teaches that the same effect will be obtained by the oral administration of a water soluble oligomer.

As discussed above, in the prior art references, β-hydroxybutyric acid oligomers of low polymerization degree or β-hydroxybutyric acid derivatives such as esters thereof were administered and the elevation of the blood levels of ketone bodies were confirmed. Considering the fact that the blood levels of ketone bodies were elevated soon after the administration, the oligomer of β-hydroxybutyric acid or the like might be hydrolyzed and absorbed in the stomach or small intestine; or the oligomer or the like is absorbed and transported into the blood and hydrolyzed there. That is, the ketone bodies administered in the prior art references must be water soluble. In addition, Non-Patent Literatures 1 and 2 also confirms that the compound to increase the blood levels of ketone bodies must be water soluble.

The applicant had shown in Patent Literature 5 that when a water insoluble polymer of β-hydroxy short-medium chain fatty acid is administered orally, the polymer will be delivered to the large intestine without being degraded in the stomach or short intestine, and degraded by the large intestinal bacterial flora to give the biological effect.

Patent Literature 1: JP 2000-515510A
Patent Literature 2: JP2002-521330A
Patent Literature 3: JP H10-95730A
Patent Literature 4: JP 2002-524506
Patent Literature 5: WO2005/021013
Non-Patent Literature 1: Veech, Prostaglandins, Leukotrienes and Essential Fatty Acids 70 (2004) 309-319
Non-Patent Literature 2: Rich, Proceedings of the Nutrition Society (1990) 49, 361-373

The above documents are herein incorporated by reference.

DISCLOSURE OF INVENTION

Problem to be Solved by the Invention

An object of the present invention is to provide a composition for promoting the production of ketone body that can promote the generation of ketone body in a sustained manner in a subject by administering a relatively small amount of said composition to the subject.

Means to Solve the Problem

The present invention provides a composition for promoting the production of ketone bodies comprising a water insoluble polymer of a β-hydroxy short-medium chain fatty acid.

The composition for promoting the production of ketone body is administered by oral administration or a procedure parallel to oral administration.

The present invention further provides a method for promoting the production of ketone body in a subject, which comprises administering a water insoluble polymer of a β-hydroxy short-medium chain fatty acid by oral administration or a procedure parallel to oral administration to the subject in need thereof.

When a poly(β-hydroxy short-medium chain fatty acid) is administered, the polymer is hardly degraded or only a small amount of the polymer is degraded at stomach or short intestine, and almost all the administered polymer reaches the large intestine. The polymer is then degraded by the bacterial flora in the large intestine to give a water soluble monomer or oligomer of β-hydroxy short-medium chain fatty acid, absorbed from the large intestine, and exhibits various physiological effects (Patent Literature 5).

When a diet comprising 5 wt % of the composition for promoting ketone body production of the present invention is given to a rat, the blood ketone body level in the rat is not significantly different from that in a rat given with the control diet containing no composition of the invention until 12 hours. However, when the rat received the same diet continuously, mild elevation of the blood levels of acetoacetate and hydroxybutyric acid was observed 2 weeks after the start administration. Different from the prior art references in which the blood ketone body level is significantly elevated for several hours soon after the administration, the composition of the present invention can mildly elevate the blood ketone body level and kept it for long term. This mild elevation of the blood ketone body level is suggested to be effective for preventing the onset of cerebral stroke in stroke-prone spontaneously hypertensive rat. In addition, the composition is also exemplified to effectively treat human patients suffered from aftereffects of cerebral stroke after several days from the start of the treatment. The inventor does not want to bind the present invention with theory, the poly(β-hydroxy short-medium chain fatty acid) degraded and absorbed in the large intestine is not transported directly into the blood, but stimulate by some mechanisms the generation of ketone bodies in the liver after it is absorbed or is used as a energy source by large intestinal bacterial flora and/or the large intestine endothelial cells.

The composition of the present invention promotes the production of ketone bodies by administering the same by means of oral administration or a procedure parallel to oral administration. Accordingly, the composition of the present invention is useful for the prevention or treatment of various diseases that can be prevented or treated by promoting the production of ketone bodies. That is, the composition for promoting ketone body production of the present invention is useful for the treatment or prevention of a disease or condition for example a neurodegenerative disease selected from the group consisting of Alzheimer's disease, fronto-temperal degeneration associated with Pick's disease, vascular dementia, senile dementia of Lewy body type, dementia of Parkinsonism with frontal atrophy, progressive supranuclear palsy and corticobasal degeneration, Down's syndrome associated Alzheimer's disease, myasthenia gravis, and muscular dystrophy; a disease or condition selected from the group consisting of amyotrophic lateral sclerosis, epilepsy, Parkinson's disease, free radical disease, heart failure, myocardial infarction, angina pectoris, type II diabetes mellitus, lack or blockage of pyruvate dehydrogenase, inactive glycolysis in one or more types of cells and Duchenne muscular dystrophy, genetic deficiency that affect badly on cellular metabolism, insulin resistance or the other deficient in glucose metabolism or the state inviting deficient in glucose metabolism and GABA preventing attack; suppressing or treating a brain disease associated with ischemia or head injury; and recovering brain function selected from the group consisting of preventing cerebral edema, protecting brain function, controlling cerebral metabolism, and lowering the degree of cerebral stroke.

The composition of the present invention is especially useful for treating and/or preventing diseases that are caused by damaged cerebral cells, especially for treating and/or preventing cerebral stroke. Further, the composition of the present invention is also useful for promoting recovery from aftereffects of cerebral stroke.

BEST MODE FOR CARRYING OUT THE INVENTION

In the present invention, "β-hydroxy short-medium chain fatty acid" represents saturated fatty acid having 3-12 carbon atoms. Preferred examples may include β-hydroxybutyric acid, β-hydroxypropionic acid, β-hydroxyvaleric acid, β-hydroxycaproic acid, β-hydroxycaprylic acid and β-hydroxycapric acid.

According to the present invention, "polymer of a β-hydroxy short-medium chain fatty acid" or "poly(β-hydroxy short-medium chain fatty acid)" may be either a homopolymer of a monomer as above or a copolymer of two or more β-hydroxy short-medium chain fatty acids. Especially, homopolymer of β-hydroxybutyric acid or a copolymer of β-hydroxybutyric acid and one or more of the other β-hydroxy short-medium chain fatty acid monomers may preferably be used. As copolymers, a copolymer of β-hydroxybutyric acid and β-hydroxyvaleric acid is preferably used.

According to the present invention, the poly(β-hydroxy short-medium chain fatty acid) may comprise any monomer unit other than β-hydroxy short-medium chain fatty acid as long as said monomer unit will not impair the physiological property of monomer or oligomer of the β-hydroxy short-medium chain fatty acid.

According to the present invention, the polymerization degree of the poly(β-hydroxy short-medium chain fatty acid) is not limited as long as the polymer is insoluble to water. When the polymer is water soluble, the orally administered polymer will be absorbed as it is or after hydrolyzed under the acid or alkaline condition in the stomach or small intestine before the polymer reaches the large intestine, and will not exert the effect of the present invention.

Polymers of a β-hydroxy short-medium chain fatty acid with about 10 or more degree of polymerization are water insoluble. For example, in the case of a poly(β-hydroxybutyric acid) is used, polymers having 1000 or more weight-average molecular weight, especially 1500 or more weight-average molecular weight are preferably used. The upper limit of the molecular weight of the polymer is not limited and any polymers which can be prepared may be used in the present invention. For example, see Appl. Microbiol. Biotechnol., 47, 140-143 (1997) (the cited reference is herein incorporated by reference) discloses that poly(β-hydroxybutyric acid) having weight average molecular weight of 20,000,000 or more was obtained. According to the present invention, the poly(β-hydroxy short-medium chain fatty acid) with polymerization degree of 20-100,000, especially 20-20,000 are preferably used.

According to the present invention, the poly(β-hydroxy short-medium chain fatty acid) may be prepared by any procedure known to the art. For example, (β-hydroxy short-medium chain fatty acid monomer, the starting material, may be polycondensed by means of a conventional polyester synthesizing method.

According to the present invention, poly(β-hydroxy short-medium chain fatty acid) produced by microorganisms or higher organisms may also be used.

There are many bacteria that produce poly(β-hydroxy short-medium chain fatty acid). For example, see Microbiol. Rev., 54, 450-472 (1990) and Biotechnol. Bioeng., 49, 1-14 (1996), those cited references are incorporated herein by reference. Polymers produced by those bacteria may also preferably be used. Poly(β-hydroxy short-medium chain fatty acid) produced by those bacteria may be isolated from the bacterial cells or may be used together with the cells. In general, bacteria contain a lot of protein and therefore, the composition comprising the polymer together with the cells will be preferable for manufacturing animal feeding stuffs or functional foods.

Among the known microorganisms, *Ralstonia eutropha* and *Alcaligenes latus* have been known to produce a large amount of poly(β-hydroxybutyric acid). Especially, *Ralstonia eutropha* cells having high protein content also contains higher amount of amino acids such as serine and glycine, which are added for the purpose of growth promotion, and therefore had been proposed as protein source. Accordingly, this microorganism will be useful not only for providing poly(β-hydroxybutyric acid) or the like, but also as protein source and are preferable especially for manufacturing animal feeding stuffs or food products.

The poly(β-hydroxy short-medium chain fatty acid) used in the present invention may be those produced by Spirulina. Spirulina is a cyanobacterium that occurs naturally in tropical and subtropical freshwater lakes. Those obtained in lake Chad in Africa and lake Texcoco in Mexico were utilized as food for long time by the native people. In these days, spirulina has been available on the market as a high nutrient health food product that contains high proteins, high minerals and high vitamins.

Spirulina obtained on the market as a health food product usually comprises about less than 0.1 wt % of poly(β-hydroxybutyric acid) based on the dry weight of the product. In the present application, spirulina that contains higher amount of poly(β-hydroxybutyric acid) can be obtained by adjusting the culture condition of the spirulina (for example, see J. Biotechnol., 172, 2791-2792 (1990), the content of the cited reference is herein incorporated by reference). According to the present invention, the poly(β-hydroxy short-medium chain fatty acid) may be those isolated from spirulina or the composition of the present invention may comprise spirulina as a whole.

Spirulina comprising an elevated amount of poly(β-hydroxy short-medium chain fatty acid) may be those comprising equal to or more than 0.2 wt %, preferably, equal to or more than 1 wt % and more preferably, equal to or more than 3 wt % of poly(β-hydroxy short-medium chain fatty acid) based on the dry weight. Spirulina containing higher amount of poly(β-hydroxy short-medium chain fatty acid) are more preferable. If it is possible to obtain spirulina comprising higher amount of poly(β-hydroxy short-medium chain fatty acid), there is no upper limit of the amount of the polymer in spirulina. For example, spirulina comprising equal to or more than 20 wt %, and for example, up to 40 wt % of poly(β-hydroxybutyric acid) based on the dry weight can be used preferably.

Gene recombinant techniques enabling a microorganism or a plant which does not originally produce the desired polymer to produce the poly(hydroxy fatty acid) have been developed (J. Bacteriol., 170, 4432-4436, 5837-5847 (1988) and Science, 256, 520-523 (1992), the cited references are herein incorporated by reference). The poly(β-hydroxy short-medium chain fatty acid) used in the present invention may be those obtained from recombinant microorganisms or plants. The polymer may be isolated from the microorganism or plant before adding to the composition of the invention, or the microorganism or plant per se containing the polymer may be added to the composition.

The composition for promoting ketone body production of the present invention can promote the production of ketone bodies in an animal body. According to the present invention, the "animal" represent not only mammals including human but also the other vertebrates including fishes and birds.

Various bacteria living in the large intestine of vertebrates form the bacterial flora and the bacteria metabolize the food stuffs which are not degraded in the stomach or short intestine, by means of fermentation to give short chain fatty acids and the like. The vertebrates absorb thus generated short chain fatty acids and utilize them for their energy or nutrition. (J. Exp. Zool. Suppl. 3, 55-60 (1989); Physiol. Rev., 78, 393-427 (1998)). Bacterial flora in the large intestine have been studied in various vertebrates including not only mammals such as human, pig and sheep but also birds such as chickens and ducks and fishes such as carps. The vertebrates, in general, have been revealed to have bacterial flora in the intestine. (Physiol. Res., 47, 259-263 (1998); Comp. Biochem. Physiol. A: Mol. Integr. Physiol., 131, 657-668 (2002); Comp. Biochem. Physiol. A: Mol. Integr. Physiol., 132, 333-340 (2002); and Appl. Environ. Microbiol., 68, 1374-1380 (2002), the cited references are herein incorporated by reference.) Accordingly, the composition of the present invention is useful for all vertebrates and especially, for mammal, bird and fish.

According to the present invention, "oral administration or a procedure parallel to oral administration" include administration via transnasal tube, gastric administration such as administration directly to stomach or infusion directly into the large intestine in addition to oral administration.

According to the present invention, the composition comprising poly(β-hydroxy short-medium chain fatty acid) is administered orally or by a procedure parallel to oral administration. Oral administration is easier and practically preferable. As was reported by the present inventor in Patent Literature 5, in the animal body, poly(β-hydroxy short-medium chain fatty acid) will be degraded by the bacterial flora in the large intestine. Accordingly, when the composition of the present invention is administered orally, the composition will not be degraded or absorbed in the small intestine to increase the serum ketone body concentration, but the polymer will be delivered to the large intestine, degraded there and then utilized.

The water soluble monomers and oligomers produced by the degradation of the poly(β-hydroxy short-medium chain fatty acid) of the present invention are degraded, absorbed or utilized in the large intestine and as a consequence, may stimulate the production of ketone bodies in the liver. Since the composition stimulates the production of ketone bodies, when poly(β-hydroxybutyric acid) is administered, mild elevation of the blood levels of acetoacetate and β-hydroxybutyric acid are observed at least 12 hours, and especially several days after the start of the administration.

On the other hand, as was shown in Patent Literature 5, no adverse side effect was observed when the poly(β-hydroxy short-medium chain fatty acid) was administered for long term. Accordingly, the composition for promoting ketone body production can be administered for preventing or treating a disease to a subject in need thereof as well as for keeping the healthy condition to a normal subject.

It has been known that the poly(β-hydroxy short-medium chain fatty acid) used in the present invention presents in the cell membrane and mitochondria of eukaryotes. It has also been known that in animal blood, poly(β-hydroxy short-medium chain fatty acid) is associated with albumin or the like (Eur. J. Biochem., 224, 317-328 (1994)).

By oral administration of the composition for promoting ketone body production according to the present invention, various disease or conditions that have been treated by promoting the production of ketone body can be treated or prevented. The composition is also useful to retain good health. Examples of the diseases include neurodegenerative diseases such as Alzheimer's disease, fronto-temporal degeneration associated with Pick disease, vascular dementia, senile dementia of Lewy body type, dementia of Parkinsonism with frontal atrophy, progressive supranuclear palsy, corticobasal degeneration, Down's syndrome associated Alzheimer's disease, myasthenia gravis and muscular dystrophy; amyotrophic lateral sclerosis, epilepsy, Parkinson's disease, free radical disease, heart failure, myocardial infarction, angina pectoris, type II diabetes mellitus, lack or blockage of pyruvate dehydrogenase, inactive glycolysis in one or more types of cells and Duchenne muscular dystrophy, genetic deficiency that affect badly on cellular metabolism, insulin resistance or the other deficient in glucose metabolism or the state inviting deficient in glucose metabolism and GABA preventing attack; and for recovering brain function including: preventing or treating the brain disease induced by head injury, preventing cerebral edema, protecting brain function, controlling cerebral metabolism, and lowering the degree of cerebral stroke.

The composition of the present invention is especially useful for treating and/or preventing various diseases that are associated with damaged cerebral cells, especially for treating and/or preventing cerebral stroke. In addition, the composition of the present invention is useful for promoting recovery from an aftereffect of cerebral stroke for example, paralysis, numbness, pain, language disorder, visual disorder, sensory disorder, urinary incontinence and emotional disorder, and especially useful for the restoration from paralysis, numbness, pain and urinary incontinence.

The composition of the present invention comprising a poly($\beta$-hydroxy short-medium chain fatty acid) may be added to diet or drinking stuff for raised or cultivated mammals, birds or fishes, or may be formulated as an additives for those feeding or drinking stuffs.

The composition of the present invention may also be used as functional food product for keeping and controlling the health state and for preventing diseases. In the present application, the term "functional food product" may include supplements, enteral nutritional product, component nutrition product, medical food product, post operative diet, foodstuffs for elder people, pregnant women, or women in lactation period and infants and additives thereto. The functional food product may be not only for human but also for animals other than human such as companion animals and livestock animals.

Embodiments wherein the composition of the present invention is provided as a pharmaceutical composition for treating a specific disease, as functional food product for preventing specific diseases or general health maintenance in animals including human and as additive for food or animal feeding product are also included in the scope of the present invention.

When the composition of the present invention is provided as a pharmaceutical composition or functional food product for an animal including human, it may be formulated as a dosage form suitable for oral administration such as powder, granule, tablet, capsule, sublingual tablet, troche, chewable tablet, dispersion and the like. The dosage form may be manufactured in a conventional manner. The composition of the present invention may be incorporated in food and/or beverage and administered orally.

The composition of the present invention may further comprise a pharmaceutically acceptable additive. Additives are not limited and may be selected from those disclosed in general reference books on drug formulation such as excipient, diluent, expander, solvent, lubricant, adjuvant, binder, disintegrating agent, coating agent, capsulation agent, emulsifier, dispersant, suspending agent, thickener, tonicity agent, buffering agent, soothing agent, preservative, antioxidant, corrigent, flavor and colorant based on the requirement.

The composition of the present invention may further comprise the other pharmaceutically active ingredient as long as it will not impair the object of the present invention.

In the case where the composition of the present invention is manufactured as animal feeding stuff, the ingredients of the composition is not limited and may be prepared by adding the poly($\beta$-hydroxy short-medium chain fatty acid) to a conventional feeding stuff product. The feeding stuff according to the present invention may comprise further physiologically active ingredient unless it impairs the object of the present invention.

The composition of the present invention may also be formulated as an additive for animal feeding stuff.

In the case the polymer used in the present invention is that manufactured by microorganism, cyanobacteria such as Spirulina, or a higher organism such as plants, the composition of the present invention may comprise whole microorganisms, cyanobacteria or higher organisms such as plant containing the poly($\beta$-hydroxy short-medium chain fatty acid) therein. When the composition comprises the whole microorganism or the like, the microorganism, cyanobacteria or higher organisms per se will be utilized as nutrient sources.

According to the present invention, the amount of poly($\beta$-hydroxy short-medium chain fatty acid) in the composition is not limited and may be determined depending on the species, body weight, sex, health condition of the subject to be administered, object of the administration and the like. In general, the amount per day may be 1 mg-500 mg/kg body weight. The composition of the present invention may be administered all at once or in two or more divided doses. Alternatively, the feeding, drinking or food stuff may be supplemented with 0.01-20 wt %, preferably, 0.1-10 wt % of the composition of the present invention and provided to the subject. The amount may be increased or decreased according to the object of the administration.

In another aspect of the present invention, a composition for promoting ketone body production comprising a $\beta$-hydroxy short-medium chain fatty acid, an oligomer thereof, or a physiologically acceptable derivatives thereof in a manner that the component is delivered to the large intestine. In this embodiment, "oligomer of $\beta$-hydroxy short-medium chain fatty acid" represents a water soluble oligomer unless otherwise indicated. Examples of preferred oligomers are those with a polymerization degree of less than 10, more preferably less than 6 and especially less than 3.

The phrase "physiologically acceptable derivative" may include acceptable salts and physiologically hydrolyzable derivatives, such as esters and amides of the $\beta$-hydroxy short-medium chain fatty acid or its oligomer and phosphorylated compounds wherein the hydroxy groups of $\beta$-hydroxy short-medium chain fatty acids are phosphorylated.

Salts may be those with an inorganic ion or an organic base. Examples of inorganic ions may include cations of alkali metals, alkali earth metals and transition metals, for example sodium, potassium, magnesium, calcium, zinc, iron and manganese cations. Examples of organic bases may include trimethyl amine, triethyl amine, ethanol amine, diethanol amine, triethanol amine, and basic amino acids such as arginine, lysine and ornithine.

Examples of esters may include alkyl esters such as methyl ester, ethyl ester and isopropyl ester, and hydroxyalkyl esters such as hydroxyethyl ester. In addition, esters with saccharides such as mono saccharides and oligo-saccharides and those with polyols such as glycol, glycerol, polyethylene glycol and polypropylene glycol are also used preferably in the invention.

Further, phosphate esters with a phosphoric acid such as nucleotides may also be used preferably.

As amides, alkyl amides such as diethyl amide and amides with oligopeptides are preferably used.

Examples of "composition for delivering a $\beta$-hydroxy short-medium chain fatty acid monomer or a oligomer thereof to the large intestine" used in the present invention may include preparations comprising a $\beta$-hydroxy short-medium chain fatty acid monomer or a oligomer thereof that is formulated as enteric coated preparation, controlled release preparation or capsule preparation that can release the component in the large intestine.

When a poly($\beta$-hydroxy short-medium chain fatty acid) is administered orally, it is decomposed into $\beta$-hydroxy short-medium chain fatty acid monomer or oligomer thereof in the large intestine by bacterial flora in the large intestine (Patent Literature 5). The "composition for delivering a $\beta$-hydroxy short-medium chain fatty acid monomer or an oligomer thereof to the large intestine" will act similarly as the composition of the present invention comprising a poly(β-hydroxy short-medium chain fatty acid). Accordingly, the composition for delivering a β-hydroxy short-medium chain fatty acid monomer or an oligomer thereof can be used for the same purpose and similar amount as the composition of the present invention comprising a poly(β-hydroxy short-medium chain fatty acid).

The present invention will be further explained by the examples below.

Example 1

Molecular Weight, Water Solubility and Hydrolyzability of the Polymer

Copolymer of β-hydroxybutyric acid and β-hydroxyvaleric acid: weight average molecular weight (Mw) according to GPC measurements against polystyrene standard Mw=560,000, number average molecular weight Mn=238,000, β-hydroxyvaleric acid=5.4 mol % (NMR): PHBV-1) was used. Ten (10) grams of the copolymer was dissolved in 250 ml of chloroform and 2 ml of concentrated hydrochloric acid was added thereto, and the mixture was heated for 7 hours under reflux. Then, 6.4 ml of 30% aqueous hydrogen peroxide was added thereto and heated more 8 hours under reflux. After that, the resulting reaction mixture was washed with water until the mixture became neutral. The chloroform phase was obtained and evaporated to give the polymer PHBV-2. The obtained polymer was analyzed with gel permeation chromatography (GPC HLC-8020/TSKgel MultiporeHXL-M Column, Tosoh Corporation) and determined as weight average molecular weight Mw=13,600 and number average molecular weight (polystyrene standard) Mn=5,600.

Eight (8) grams of the obtained PHBV-2 was dissolved in 200 ml of chloroform. The mixture was treated two times by being added with 2.56 ml of 30% aqueous hydrogen peroxide and heated under reflux for 8 hours each. The product was collected in the same manner as above to give PHBV-3. Mw=37000 and Mn=1250 (polystyrene standard).

Two (2) grams of the obtained PHBV-3 was dissolved in 50 ml of chloroform and 0.2 ml of concentrated hydrochloric acid was added thereto. The mixture was treated four times by being added with 0.64 ml of 30% aqueous hydrogen peroxide and heated under reflux for every 4 hours each heated twice under reflux for every 4 hours. The product was collected to give PHBV-4. Mw=860 and Mn=490 (polystyrene standard).

About 100 mg of each PHBV-1-PHBV-4 was weighted precisely, put in 50 ml of water at 37° C. and stirred for 6 hours. After that, PHBV-1, PHBV-2 and PHBV-3 were collected by filtration and dried and then, weighted. The reduction of the weight from the weight put into water was less than 4%. That is, the difference between the weight of the polymers before and after soaked in water was within the error range and PHBV-1, PHBV-2 and PHBV-3 were evaluated as water insoluble. In contrast, almost all PHBV-4 put in water was dissolved after 2 hours (confirmed with the eye) and PHBV-4 was evaluated as water soluble.

With respect to PHBV-1, PHBV-2 and PHBV-3, that were confirmed as water insoluble, hydrolytic property and degradability by enzyme in the stomach and small intestine were determined.

About 100 mg of each PHBV-1, PHBV-2 and PHBV-3 was weighted and added to 50 ml of each aqueous enzyme solution containing 0.1 wt % of the enzyme and adjusted to the pH mimicking the stomach or small intestine environment. The mixture was shaken at 37° C. for the predetermined time, i.e. 6 hours for mimicking the stomach digestion and 10 hours for mimicking the short intestine digestion, and then, filtered and collected. In each of PHBV-1, PHBV-2 and PHBV-3, 96% or more of the added polymer was observed after the digestion in the stomach or small intestine mimicking atmosphere. No significant degradation of the polymer was observed.

The inventors confirmed by this test that the composition of the present invention are hardly degraded by the acidic or alkaline atmosphere or digestive enzymes in the stomach and small intestine.

Enzyme solutions used in this example were as follows:
Pepsin: Dissolved in gastric Juice mimetic solution (aqueous hydrochloride pH=1.5)
Amylase: Dissolved in gastric juice mimetic solution (aqueous hydrochloride pH=5.5 comprising calcium chloride 0.03 wt %)
Trypsin: Dissolved in small intestinal Juice mimetic solution (aqueous sodium hydrogen carbonate pH=8.0)
Lipase: Dissolved in small intestinal juice mimetic solution (aqueous sodium hydrogen carbonate pH 7.5, comprising calcium chloride 0.03 wt %)

Example 2

Change of Concentration of Copolymer of β-hydroxybutyric Acid and β-hydroxyvaleric Acid in the Blood Animals: 8-weeks old male Spragure-Dawley SPF rat (Japan SLC, Inc. Hamamatsu, Japan) (n=3)
Control Diet: Commercially available powdery diet CE-2 (CLEA Japan, Inc. Tokyo, Japan).
Water: The animals received water ad libitum. Atmosphere: Temperature 23° C., humidity 50%, lighting with fluorescent lamp from 8:00 to 20:00 every day.

Procedure: After the first acclimatization period (4 days), the animals were divided into two groups and the animals were further acclimated by the control diet ad libitum from 10:00-17:00 for 7 days. At the starting day, just before feeding, peripheral blood was collected from the tail. The control animals were fed with the control diet and the test animals were fed with the control diet supplemented with 5 wt % of the copolymer of β-hydroxybutyric acid and β-hydroxyvaleric acid (Mw=560000, β-hydroxyvaleric acid=5.4 mol %, PHBV-1) on 10:00-17:00 every day. Every 4 hours, peripheral blood was obtained from the tail of the animals and the concentration of β-hydroxybutyric acid in the blood was observed. The concentration of β-hydroxybutyric acid in blood was determined by a conventional method. Namely, serum was isolated from the obtained blood, diluted with PBS (pH7.4) and subjected to the enzyme cycling method at Japan Clinical Laboratories, Inc. (Kyoto, Japan).

Result: The β-hydroxybutyric acid concentration in the blood obtained just before feeding (time 0) was increased. This might be due to the utilization of β-hydroxybutyric acid as an energy source under fasting conditions (after 17 hours fasting). The animals received the diet comprising PHBV-1 ad libitum for 7 hours and the blood β-hydroxybutyric acid concentrations of the animals during the period of feeding and up to 12 hours from the start of the feeding were not significantly different between the control group and the test group.

TABLE 1

| | blood concentration of β-hydroxybutyric acid: μmol/L | | | |
|---|---|---|---|---|
| | 0 h | 4 h | 8 h | 12 h |
| control | 221 ± 88 | 148 ± 17 | 108 ± 14 | 103 ± 6 |
| test | 247 ± 95 | 126 ± 25 | 110 ± 26 | 106 ± 29 |

Example 3

Promotion of Ketogenesis

Animals: 8-weeks old male Sprague-Dawley SPF rat (Japan SLC, Inc. Hamamatsu, Japan) (n=3) were used.

Control Diet: Commercially available powdery diet CE-2 (CLEA Japan, Inc. Tokyo, Japan) was used.

Water: The animals received water ad libitum.

Atmosphere: Temperature 23° C., humidity 50%, lighting with fluorescent lamp from 8:00 to 20:00, every day.

Procedure:. After the first acclimatization period (4 days), the animals were divided into two groups. The control group animals received the control diet ad libitum and the test animals received the control diet supplemented with 5 wt % of PHBV-1 ad libitum for two weeks. In the morning of the last day, the animals were dissected and the serum was obtained from the arterial blood collected from the abdominal aorta. The liver was minced, mixed well, and 0.1 g of the same was put in a microtube. 0.9 ml of PBS (pH 7.4) supplemented with 0.1 mM EDTA2Na was added to the microtube and the liver tissue was homogenized on ice. The microtube was then centrifuged and the supernatant was obtained. The amount of the ketone body, i.e. the amount of acetoacetate (AcAc) and β-hydroxybutyric acid (HB) in the serum and the supernatant were measured by means of the enzyme cycling method. The measurement was conducted by Japan Clinical Laboratories, Inc., Kyoto, Japan.

Results: The ketone bodies in the arterial blood and liver were increased after two weeks administration of PHBV-1. Since the liver cannot metabolize the ketone bodies but produce them, the increase of the ketone body concentrations suggest that the production of ketone bodies in the liver was promoted.

TABLE 2

| | Promotion of ketogenesis: μmol/L | | | |
|---|---|---|---|---|
| | HB in arterial blood | AcAc in arterial blood | HB in liver[1] | AcAc in liver[1] |
| control | 271 ± 25 | 36 ± 8 | 198 ± 25 | 23 ± 3 |
| test | 334 ± 20* | 60 ± 24 | 282 ± 30* | 38 ± 5** |

[1] homogenized liver 0.1 g + PBS 0.9 ml
*p < 0.1,
**p < 0.05

Example 4

Prevention of Cerebral Stroke

Animals: Male, 9 weeks old, stroke-prone spontaneously hypertensive rat, SHRSO/Izm (SPF) Japan SLC, Inc. were used (n=5).

Control Diet: Commercially available powdery diet SP-2 (Japan SLC, Inc. Hamamatsu, Japan) supplemented with 1 wt % sodium chloride was used.

Water: The animals received water ad libitum.

Atmosphere: Temperature 23° C., humidity 50%, lighting with fluorescent lamp from 8:00 to 20:00, every day.

Procedure: After the first acclimatization period (4 days), the animals were divided into two groups. The control group animals received the control diet ad libitum. The test animals received the control diet supplemented with 5 wt % of PHBV-1 ad libitum. The animals were bred until a symptom of cerebral stroke, such as upholding the front leg and overturning appeared. The time when the symptom of cerebral stroke first appeared was recorded.

Results:

Control Group: time period until the symptom of cerebral stroke first appeared=15, 16, 27, 35 and 36 days.

Test Group: time period until the symptom of cerebral stroke first appeared=23, 26, 31, 37 and 50 days According to the results, the times when the symptoms first appeared were apparently later in the test group than those in the control group. This results support that PHBV-1 is effective for the prevention of onset of cerebral stroke.

The stools of a test group animal that developed the symptom last were collected for one week on the 7th week, and the intestinal degradation of PHBV-1 was determined.

The collected stools were dried under vacuum, crushed, and put in chloroform and hearted under reflux for minutes to extract PHBV. Thus obtained PHBV was precipitated by adding n-hexane and collected. The amount of the collected PHBV was measured to give the amount, of PHBV contained in the stools. The degrading ratio of PHBV calculated from the intake amount and the amount in the stools was 6.0%.

Example 5

Recovery from Aftereffects of Cerebral Stroke

Subject 1: Male, age 50 subject, 4 years and 1 month had elapsed since the onset of hemorrhagic cerebral stroke, being suffered from palsies, numbness and pain on his right side and being qualified as level 2 handicapped person.

Administration of β-hydroxybutyric Acid:

The dosage form was prepared by filling poly β-hydroxybutyric acid (prepared by fermentation, weight average molecular weight: 839,000) in a No. 1 capsule shell (capacity 0.3 g). The subject received once daily one capsule.

Result:

On day 4, the subject started to feel relief from numbness sometimes. After 2 weeks, he clearly acknowledged relief from numbness and dull pain. The time period of a day when he felt no numbness or dull pain increased gradually and after 6 months, the numbness and dull pain disappeared at all.

In parallel with the relief from numbness and dull pain, he felt that the tension in the muscle or body was relaxed. Due to the relaxation, he could move the paralyzed segment at his own initiative.

The movement of the paralyzed segments was gradually improved by conducting rehabilitation and 3 months after, he realized that the paralysis in his right arm and leg alleviated and that he could perform normal daily activities by himself.

The subject had also been suffered from urinary incontinence in addition to numbness. On day 8 of administration, the number of the episodes of incontinence was suddenly declined and on day 14, the incontinence resolved.

Subject 2: Male, age 60 subject, 3 years had elapsed since the onset of hemorrhagic cerebral stroke, being suffered from palsies and dull pain on his right leg and paralysis on the right edge of his lip.

Administration of Poly 3-hydroxy Short-Medium Chain Fatty Acid:

The subject received once daily one capsule. Each capsule contains the poly β-hydroxybutyric acid as above in a No. 1 capsule shell (capacity 0.3 g).

Result: On day 8, the subject acknowledged relief from numbness and dull pain. The administration of poly β-hydroxy short-medium chain fatty acid was stopped at day 10. After that, the numbness or dull pain were not returned.

Example 6

Culture of Spirulina Containing a Large Amount of Poly β-hydroxy-Short-Medium Chain Fatty Acid

*Spirulina platensis* (0.125 g/L, dry weight) was inoculated in 18 L of Kosaric medium supplemented with 0.5 w/v % sodium acetate in a plastic container. The spirulina culture was exposed to 900-1100 lux (at the surface of the medium) light for 16 hours/day, kept at 24° C. and pH 9.3-9.6, and bubbled with air for 25 days. After that, the spirulina was collected by filtration and dried in an oven at 70° C. to give 43 g of dried spirulina.

From thus obtained spirulina, poly β-hydroxybutyric acid was extracted with chloroform and the weight ratio of the polymer in the spirulina was 3.1 wt %. The extracted compound was determined to be poly β-hydroxybutyric acid by using NMR.

Kosaric medium ingredients (g/L): $NaHCO_3$ (9.0), $K_2HPO_4$ (0.25) $NaNO_3$ (1.25), $K_2SO_4$ (0.5), NaCl (0.5), $MgSO_4.7H_2O$ (0.1), $CaCl_2$ (0.02), $FeSO_4.2H_2O$ (0.005) and trace mineral solution (0.5 ml/L)

Trace mineral solution ingredients (g/L): $H_2BO_4$ (2.86), $MnCl_2.4H_2O$ (1.81), $ZnSO_4.7H_2O$ (0.22), $CuSO_4.5H_2O$ (0.08), $MoO_3$ (0.01).

The invention claimed is:

1. A method for treating cerebral stroke in a subject in need thereof, comprising:
    administering a water insoluble polymer of β-hydroxy short-medium chain fatty acid to the subject in need thereof, wherein
        the water insoluble polymer of a β-hydroxy short-medium chain fatty acid is a homopolymer of β-hydroxybutyric acid or a copolymer of β-hydroxybutyric acid and a saturated β-hydroxy fatty acid having 3-12 carbon atoms,
        the weight average molecular weight of the water insoluble polymer of a β-hydroxy short-medium chain fatty acid is in the range of 13,600-20,000,000, and
        the water insoluble polymer of a β-hydroxy short-medium chain fatty acid is administered orally, via a transnasal tube, or by gastric administration.

2. The method of claim 1, wherein the saturated β-hydroxy fatty acid having 3-12 carbon atoms is selected from the group consisting of: β-hydroxypropionic acid, β-hydroxyvaleric acid, β-hydroxycaproic acid, β-hydroxycaprylic acid, β-hydroxycapric acid, and a mixture thereof.

3. The method of claim 1, wherein the water insoluble polymer of a β-hydroxy short-medium chain fatty acid is a homopolymer of β-hydroxybutyric acid.

4. The method of claim 1, wherein the water insoluble polymer of a β-hydroxy short-medium chain fatty acid is a copolymer of β-hydroxybutyric acid and β-hydroxyvaleric acid.

5. The method of claim 1, wherein the water insoluble polymer of a β-hydroxy short-medium chain fatty acid is produced by spirulina.

6. The method of claim 1, wherein the water insoluble polymer of a β-hydroxy short-medium chain fatty acid is administered orally.

7. The method of claim 6, wherein the water insoluble polymer of a β-hydroxy short-medium chain fatty acid is administered in the form of animal feedstuff or an additive for animal feedstuff.

8. The method of claim 6, wherein the water insoluble polymer of a β-hydroxy short-medium chain fatty acid is administered in the form of a functional food product.

9. The method of claim 6, wherein the water insoluble polymer of a β-hydroxy short-medium chain fatty acid is administered in the form of a pharmaceutical composition.

10. The method of claim 1, wherein the water insoluble polymer of a β-hydroxy short-medium chain fatty acid is orally administered for at least two weeks to the subject.

11. A method for promoting recovery from an after-effect of cerebral stroke in a subject in need thereof, comprising:
    administering a water insoluble polymer of a β-hydroxy short-medium chain fatty acid to the subject in need thereof, wherein
        the water insoluble polymer of a β-hydroxy short-medium chain fatty acid is a homopolymer of β-hydroxybutyric acid or a copolymer of β-hydroxybutyric acid and a saturated β-hydroxy fatty acid having 3-12 carbon atoms,
        the weight average molecular weight of the water insoluble polymer of a β-hydroxy short-medium chain fatty acid is in the range of 13,600-20,000,000, and
        the water insoluble polymer of a β-hydroxy short-medium chain fatty acid is administered orally, via a transnasal tube, or by gastric administration.

12. A method for reducing the severity of cerebral stroke in a subject in need thereof, comprising:
    administering a water insoluble polymer of β-hydroxy short-medium chain fatty acid to the subject in need thereof, wherein
        the water insoluble polymer of a β-hydroxy short-medium chain fatty acid is a homopolymer of β-hydroxybutyric acid or a copolymer of β-hydroxybutyric acid and a saturated β-hydroxy fatty acid having 3-12 carbon atoms,
        the weight average molecular weight of the water insoluble polymer of a β-hydroxy short-medium chain fatty acid is in the range of 13,600-20,000,000, and
        the water insoluble polymer of a β-hydroxy short-medium chain fatty acid is administered orally, via a transnasal tube, or by gastric administration.

13. The method of claim 1, wherein 1 mg/kg to 500 mg/kg of the water insoluble polymer of a β-hydroxy short-medium chain fatty acid is orally administered to the subject per day.

14. The method of claim 11, wherein 1 mg/kg to 500 mg/kg of the water insoluble polymer of a β-hydroxy short-medium chain fatty acid is orally administered to the subject per day.

15. The method of claim 12, wherein 1 mg/kg to 500 mg/kg of the water insoluble polymer of a β-hydroxy short-medium chain fatty acid is orally administered to the subject per day.

* * * * *